United States Patent [19]
Qiu et al.

[11] Patent Number: 6,133,440
[45] Date of Patent: Oct. 17, 2000

[54] PROCESS FOR THE PREPARATION OF IMMUNOMODULATORY POLYSACCHARIDES FROM ALOE

[75] Inventors: Zhihua Qiu; Belaid Mahiou, both of Westminster, Colo.

[73] Assignee: Univera Pharmaceuticals, Inc., Broomfield, Colo.

[21] Appl. No.: 09/169,449

[22] Filed: Oct. 9, 1998

Related U.S. Application Data

[60] Provisional application No. 60/061,681, Oct. 10, 1997, and provisional application No. 60/098,271, Aug. 28, 1998.

[51] Int. Cl.$^7$ .................................................. C08B 37/00
[52] U.S. Cl. ....................... 536/123; 536/123.1; 536/128; 514/54; 424/195.1; 435/99; 435/101
[58] Field of Search .................................... 536/123, 128, 536/123.1; 514/54; 435/101, 99; 424/195.1

[56] References Cited

U.S. PATENT DOCUMENTS

| | | |
|---|---|---|
| 3,470,109 | 9/1969 | Marsh . |
| 3,892,853 | 7/1975 | Cobble . |
| 4,178,372 | 12/1979 | Coats . |
| 4,555,987 | 12/1985 | Tumlinson . |
| 4,735,935 | 4/1988 | McAnalley . |
| 4,851,224 | 7/1989 | McAnalley . |
| 4,917,890 | 4/1990 | McAnalley . |
| 4,957,907 | 9/1990 | McAnalley . |
| 4,959,214 | 9/1990 | McAnalley . |
| 4,966,892 | 10/1990 | McAnalley . |
| 5,106,616 | 4/1992 | McAnalley et al. . |
| 5,118,673 | 6/1992 | Carpenter et al. . |
| 5,284,833 | 2/1994 | McAnalley et al. . |
| 5,308,838 | 5/1994 | McAnalley et al. . |
| 5,441,943 | 8/1995 | McAnalley et al. . |
| 5,443,830 | 8/1995 | Moore et al. . |
| 5,468,737 | 11/1995 | McAnalley et al. . |
| 5,512,488 | 4/1996 | Eberendu et al. . |
| 5,562,906 | 10/1996 | Terry et al. . |
| 5,587,364 | 12/1996 | McAnalley et al. . |
| 5,703,060 | 12/1997 | McAnalley et al. . |
| 5,773,425 | 6/1998 | McAnalley et al. . |
| 5,780,453 | 7/1998 | McAnalley et al. . |
| 5,786,342 | 7/1998 | Carpenter et al. . |
| 5,824,659 | 10/1998 | Strickland et al. . |

OTHER PUBLICATIONS

Boericke (1985) *Materia media with Respiratory*, 9$^{th}$ Ed., B. Jain Pub. Pvt. Ltd., New Delhi, 679.
Brown (1995) *The Herb Society of America; Encyclopedia of Herbs and Their Uses*, Dorling Kinderstey Publ. Inc., 372.
Byeon et al. (1998) J. Investigative Dermatology 110:811–817.
Chevallier (1996) *The Encyclopedia of Medicinal Plants*, Dorling Kinderstey Pub. Inc., 151.
Gowda et al. (1979) Carbohydrate Research 72:201–205.
Gowda (1980) Carbohydrate Research 83:402–405.
Grieve (1971) *A Modern Herbal*, Dover Publication, Inc., New York, 70–71.
Hranisavljević–Jakovljević and Miljković–Stojanović (1981) Bulletin de la Societe Chimique Beograd 46:269–273.
Krochmal (1973) *A Guide to the Medicinal Plants of the United States*, Quadrangle/The New York Times Book Co., New York, 238–239.
Lewis and Elvin–Lewis (1977) *Medical Botany*, John Wiley & Sons Pub. pp. 191, 243, 255, 289, 363.
Mandal and Das (1980) Carbohydrate Research 86:247–257.
Mandal and Das (1980) Carbohydrate Research 87:249–256.
Mandal et al. (1983) Indian J. Chemistry 22B:890–893.
*Merck Index* 9$^{th}$ Edition (1976) (Xanthoxylum p. 1299) (Berberine pp. 152–153) (Fagarine p. 515).
Paulsen et al. (1978) Carbohydrate Research 60:345–351.
Radjabi et al. (1983) Carbohydrate Research 116:166–170.
Radjabi–Nessab et al. (1984) Biochimie 66:563–567.
Wozniewski et al. (1990) Carbohydrate Research 198:387–391.
Yagi et al. (1984) J. Pharmaceutical Sciences 73:62–65.
Yagi et al. (1977) Planta Medica 31:17–20.
Danhof and McAnalley (Aug. 1983) Drug & Cosmetic Ind., pp. 52, 54, 105–106.
Day et al. (1922) J. Am. Pharm. Assoc. XI:462–463.
Fujita et al. (1976) Biochemical Pharmacology 25:205.
Haq and Hannan (1981) Bangladesh J. Sci. Ind. Res. XVI:68–72.
Ovodova et al. (1975) Chemical Abstracts 83:313, Ref. No. 93833a.
Robson et al. (1982) J. Burn Care Rehab. 3:157–163.
Shcherbukhin et al. (1979) A.N. Bakh Institute of Biochemistry, Academy of Sciences of the USSR, Moscow p. 666. Translated from Applied Biochemistry & Microbiology 15:892–896.
Shimizu et al. (1997) Chemical Abstracts 126:328, reference No. 126:197428v.
Smothers (Jan. 1983) Drug & Cosmetic Ind., pp. 40, 77–80.
Vilkas and Radjabi–Nassab (1986) Biochimie 68:1123–1127.
Waller et al. (1978) Proc. Okla. Acad. Sci. 58:69–76.
Waller et al. (1994) Cosmetics and Toiletries Manufacturing Worldwide 64–80.
Winters et al. (1981) Economic Botany 35:89–95.
Yagi et al. (1985) Experientia 41:669–671.

*Primary Examiner*—Francisco Prats
*Attorney, Agent, or Firm*—Swanson & Bratschun, L.L.C.

[57] ABSTRACT

The present invention provides a rapid and efficient method for the preparation and isolation of biologically active polysaccharides from Aloe. The present invention includes the activated mixture of polysaccharides (referred to herein as "Immuno-10"), produced by the methods of the invention. The invention also includes the use of the polysaccharides as immunostimulating, immunomodulating and wound healing agents. The resulting immunomodulatory complex has a higher activity and is more stable than bulk carbohydrates isolated using prior art alcohol precipitation schemes.

4 Claims, 8 Drawing Sheets

PROCESS FOR THE PREPARATION OF IMMUNOMODULATORY POLYSACCHARIDES FROM ALOE

RELATED APPLICATIONS

This application claims priority from U.S. Provisional Patent Application Ser. No. 60/061,681, filed Oct. 10, 1997, entitled "Process for Preparation of Immunomodulatory Carbohydrates from Aloe" and U.S. Provisional Patent Application Ser. No. 60/098,271, filed Aug. 28, 1998, entitled "Process for Preparation of Immunomodulatory Carbohydrates from Aloe."

FIELD OF THE INVENTION

The present application relates to methods for activating and purifying polysaccharides from Aloe. In particular, the invention relates to methods for isolating polysaccharides with immunomodulatory activity from Aloe. The present invention includes the activated mixture of polysaccharides (referred to herein as "Immuno-10" or "Immuno-10 polysaccharide"), produced by the methods of the invention. The invention also includes the use of the polysaccharides as immunostimulating, immunomodulating and wound healing agents.

BACKGROUND OF THE INVENTION

Aloe is an intricate plant which contains many biologically active substances. (Cohen et al. in *Wound Healing/Biochemical and Clinical Aspects*, 1st ed. W B Saunders, Philadelphia (1992)). Over 300 species of Aloe are known, most of which are indigenous to Africa. Studies have shown that the biologically active substances are located in three separate sections of the aloe leaf—a clear gel fillet located in the center of the leaf, in the leaf rind or cortex of the leaf and in a yellow fluid contained in the pericyclic cells of the vascular bundles, located between the leaf rind and the internal gel fillet, referred to as the latex. Historically, Aloe products have been used in dermatological applications for the treatment of burns, sores and other wounds. These uses have stimulated a great deal of research on identifying compounds from Aloe that have clinical efficacy, particularly anti-inflammatory activity. (See, e.g., Grindlay and Reynolds (1986) J. of Ethnopharmacology 16:117–151; Hart et al. (1988) J. of Ethnopharmacology 23:61–71). As a result of these studies there have been numerous reports of Aloe compounds having diverse biological activities, including anti-tumor activity, anti-acid activity (Hirata and Suga (1977) Z. Naturforsch 32c:731–734), anti-diabetic activity, tyrosinase inhibiting activity (Yagi et al. (1987) Planta medica 515–517) and antioxidant activity (International Application Serial No. PCT/US95/07404, published Dec. 19, 1996, publication number WO 96/40182).

It has also been reported that Aloe products can stimulate the immune system. The ability of Aloe to stimulate the immune system has been attributed to polysaccharides present in the gel. (See, e.g., Day et al. (1922) J. Am. Pharm. Assoc. 11:462–463; Flagg (1959) American Perfumes and Aromatics 74:27–28, 61; Waller et al. (1978) Proc. Okla. Acad. Sci. 58:69–76; Shcherbukhin et al. (1979) Applied Biochemistry & Microbiology 15:892–896; Mandal et al. (1980) Carbohydrate Research 86:247–257; Mandal et al. (1980) Carbohydrate Research 87:249–256; Winters et al. (1981) Eco. Botany 35:89–95; Robson et al. (1982) J. Burn Care Rehab. 3:157–163; Ivan et al. (1983) Drug & Cosmetic Ind. 52–54, 105–106; Smothers (1983) Drug & Cosmetic Ind. 40:77–80; Mandal et al. (1983) Indian J. of Chem. 22B:890–893; Vilkas et al. (1986) Biochimie 68:1123–1127; Waller et al. (1994) Cosmetic Toiletries Manufacturing Worldwide 64–80; U.S. Pat. No. 5,308,838 of McAnalley et al.).

Aloe products are also used extensively in the cosmetic industry to protect skin against the harmful effects of ultraviolet radiation. (Grollier et al. U.S. Pat. No. 4,656,029, issued Apr. 7, 1987). Chronic exposure of the skin to ultraviolet radiation causes skin cancer in humans and laboratory animals. Exposure of the skin of laboratory animals to ultraviolet B (UVB) radiation (280–320 nm) causes suppression of the skins immune system, which impairs its ability to develop an immune response to UV-induced skin cancers, contact-sensitizing haptens and a variety of infectious microorganism. (See, Strickland (1994) J. Invest. Dermatol. 102:197–204, and references cited therein). Studies by Strickland et al. show that topical application of Aloe vera gel reduces the suppression of the immune system caused by UVB exposure. (Strickland (1994) J. Invest. Dermatol. 102:197–204).

The ability of native gel to reduce suppression of the immune system, is very low and irregular and also decreases with time. One hypothesis is that the UV-B protective factor is hydrolyzed by naturally occurring enzymes in the Aloe plant and/or by bacterial degradation. Therefore, it would seem likely that isolating polysaccharides from Aloe would help preserve this immunomodulatory activity. Previous prior art methods for the bulk isolation of polysaccharides from Aloe, however, do not effectively preserve the immunomodulatory activity. These methods, described for example in U.S. patent application Ser. Nos. 4,957,907, 4,966,892 and 5,356,811, use lengthy (4–24 hours) alcohol precipitation and centrifugation steps. Given the failure of the prior art methods to effectively preserve the immunomodulatory activity of Aloe gel, it would be useful to have a procedure for the isolation of polysaccharides from Aloe that would allow the immunomodulatory activity to be retained and stabilized. The present invention provides such methods.

SUMMARY OF THE INVENTION

The present application relates to methods for activating and isolating a mixture of polysaccharides from Aloe. Included in the present invention is the activated mixture of polysaccharides produced and the use of said mixture as an immunostimulating, immunomodulating and wound healing agent. The activity of polysaccharides isolated by the method of this invention is much higher and much more stable and reproducible than that of native Aloe gel extracts.

The method of the present invention is comprised of (a) extracting Aloe gel juice from Aloe; (b) performing a controlled limited enzymatic hydrolysis of the total polysaccharides in said Aloe gel juice at a temperature and for a period of time suitable for limited carbohydrate hydrolysis; (c) terminating said hydrolysis; and (d) optionally decolorizing and filtering said hydrolyzed product. In a preferred embodiment the limited hydrolysis is performed by the addition of cellulase at 25° C.±1° C. for a period of 2–2.5 hours using a ratio of 0.5 g–2.5 g of cellulase to 216 L of gel extract. A schematic diagram of the instant method is provided in FIG. 1.

The present invention includes the mixture of polysaccharides (referred to herein as "Immuno-10" or "Immuno-10 polysaccharide") prepared and isolated by the methods of this invention. Said composition of matter is characterized in detail below.

The present invention also includes the use of Immuno-10 as an immunostimulating, immunomodulating and wound healing agent. Immuno-10 prevents suppression of contact hypersensitivity (CH) in mice exposed to UVB radiation and also inhibits UVB irradiation-induced tumor necrosis factor (TNF-α) release in human epidermoid carcinoma cell line. The Immuno-10 isolated by the method of this invention can be used in an oral or topical formulation for the restoration or stimulation of the human immune system, for individuals suffering immunodeficiency or immune-suppressing diseases or for therapeutic treatment for diseases, such as HIV. The Immuno-10 isolated by the method of this invention is also useful for wound healing. The polysaccharides isolated by the method of this invention are more active and more stable than native Aloe gel.

The methods described herein include a limited and controlled hydrolysis of Aloe polysaccharides, which operates to increase the stability and immunomodulatory activity of Aloe polysaccharides. The method is faster, simpler and more amenable to scale-up than prior art methods, and does not involve the use of organic solvents. Moreover, the processes described herein increase the solubility of Aloe polysaccharide and reduce the viscosity of solutions thereof without loss of the immunomodulatory activity. Immuno-10 isolated using the method of this invention shows qualitatively-similar UVB protective activity as the activated bulk polysaccharide purified from the same Aloe gel extracts, but has a higher specific activity than the bulk polysaccharide. Additionally, the purified Immuno-10 exhibits UVB CH restorative activity that is at least twice as high as that of native Aloe gel.

It is to be understood that both the foregoing general description and the following detailed description are exemplary and explanatory only and are not restrictive of the invention as claimed.

DETAILED DESCRIPTION OF THE INVENTION

The present application is drawn to methods for activating and isolating a defined biologically active mixture of polysaccharides from Aloe. The term "Aloe" refers to the genus of plants found worldwide from the Liliaceae family of which the *Aloe barbadensis* plant is a species. The method of the present invention is comprised of (a) extracting Aloe gel juice from Aloe; (b) performing a limited and controlled hydrolysis of the total polysaccharides in said Aloe gel juice at a temperature and for a period of time suitable for limited carbohydrate hydrolysis; (c) terminating said hydrolysis; and (d) optionally decolorizing and filtering said hydrolyzed product.

Figure 1:
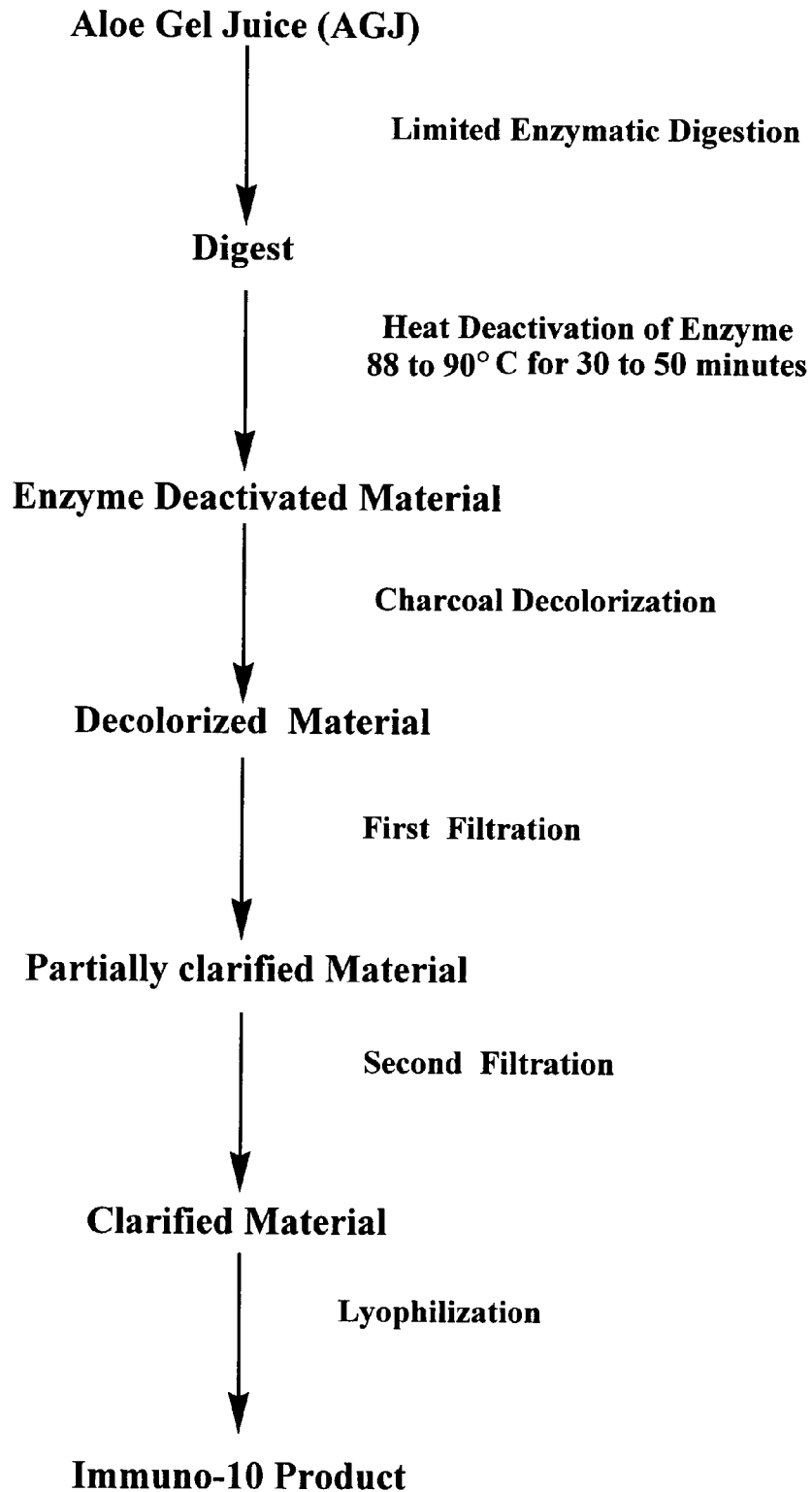
FIG. 1 illustrates schematically the general method of the present invention for the preparation of Immuno-10 from Aloe.

A schematic diagram of the instant method is provided in FIG. 1. With reference to FIG. 1, Aloe gel juice (AGJ) is produced from fresh gel fillets by any method known in the art, including but not limited to grinding, using a "Thompson Aloe Juice Extractor" (Thompson Manufacturing Co., Harlingen, Tex.) or using pressure rollers. The AGJ is then mixed with a hydrolyzing agent. Examples of hydrolyzing agents include but are not limited to enzymes, such as cellulase, pectinase or mannanase and non-enzymatic hydrolyzing agents, such as hydrochloric acid and trifluoroacetic acid. In a preferred embodiment the hydrolyzing agent is an enzyme. Most preferably the hydrolyzing agent is a cellulase, such as cellulase 4000 (Valley Research Inc.). The resulting mixture is allowed to incubate at a temperature and for a length of time suitable for limited carbohydrate hydrolysis (see Example 1). For example when the hydrolyzing agent is cellulase this is preferably 2–2.5 hours at 25° C.±1° C. using a ratio of 0.5 g to 2.5 g of cellulase to 216 L of gel extract (see Example 4).

Carbohydrate hydrolysis is then stopped after the appropriate period of time. If a cellulase is used, this is accomplished preferably by heating the digestion mixture to a high temperature. The resulting Immuno-10 has a red color at this stage, and this color may optionally be removed by mixing the Immuno-10 with charcoal particles to form a slurry (see Example 1) or by column chromatography. Examples of suitable chromatography resins, including but not limited to reverse-phase resins. Examples of reverse phase resins, include but are not limited to aromatic resins, such as the XAD series of resins and CG-161 and non-aromatic resins, such as C-4, C-8 and C-18. In preferred embodiments, such Immuno-10 slurry is filtered in order to remove the charcoal particles. This can be accomplished by any of the methods known in the art. Preferred embodiments of the invention use a multistep filtration scheme, in which the slurry is passed through a series of filters of progressively smaller pore sizes (see Example 1 and Tables 1 and 2). For example, in some embodiments, the slurry is filtered over 30 μm filter paper, then over 1.0 μm filter paper, and finally over 0.7 μm filter paper. In some embodiments, a filtration aid, such as a celite, FW12 or Fw14 is included in the mixture to be filtered. Following filtration using this method, the filtrate is decolorized and free of fine charcoal particles.

Figure 2:
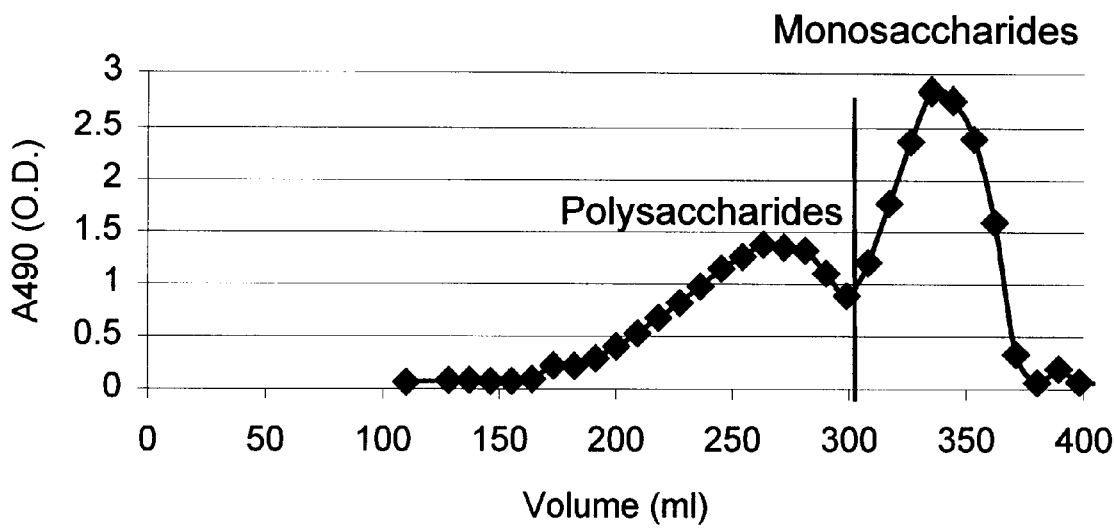
FIG. 2 depicts a chromatogram of Immuno-10, following limited enzyme hydrolysis, decolorization and filtration (Example 1). The chromatography was performed on a on a Sepharose CL-4B column, monitoring absorbance at 490 nm using the phenol sulfuric acid method.

Following the optional decolorization and filtration, the Immuno-10 may be dried for storage by lyophilization or spray-drying. Typical yields using the instant method are approximately 6 g of lyophilized solids per liter of AGJ. Chromatography of Immuno-10 on a Sepharose CL-4B column reveals that it contains both polysaccharide and monosaccharide fractions as evidenced by the presence of two carbohydrate peaks at 490 nm (FIG. 2). Although the immune regulating activity is contained within the polysaccharide peak, the monosaccharides do not affect this activity (data not shown). The monosaccharides can be removed by diafiltration/dialysis of AGJ prior to the limited enzymatic digestion.

Examples 2 and 3 describe methods for the preparation of pharmaceutical grade Immuno-10, which is a purer form of Immuno-10 having greater biological activity and stability.

Included in the present invention is the activated polysaccharide (referred to herein as "Immuno-10" or "Immuno-10 polysaccharide"), produced by the methods of the invention.

The composition and chemical structure of the activated polysaccharides in Immuno-10 was determined using pharmaceutical grade Immuno-10 having a purity of >95% and is as follows:

Size exclusion chromatography analysis shows that the average molecular weight of the polysaccharides in Immuno-10 is 70~80 kDa with a range between 50~200 kDa. The molecular weight was determined using size exclusion chromatography on a Sephadex G-100 column and HPLC gel permeation on a Superose 12 column (H10/30 Pharmacia).

Analysis of the monosaccharide composition indicates that the polysaccharides in Immuno-10 contain D-galactose (approx 5% or less), D-glucose (approx. 5% or less) and D-mannose (approximately 90%). The polysaccharides in Immuno-10 may also contain trace amounts of xylose and arabinose.

Pharmaceutical grade Immuno-10, which is more highly purified (see Examples 2 and 3), contains mainly D-galactose and D-mannose in a ratio of 1 to 9.6±2.2.

Proton and $^{13}$C NMR-spectroscopy analysis indicates that the monosaccharide linkages are primarily β-1,4 linkages. The proton and $^{13}$C-NMR spectra were analyzed on a Varian XL-300 spectrometer. The main structure of Immuno-10 polysaccharide is β-1,4 glucomannan. Furthermore, the polysaccharide is highly acetylated (approximately 1 acetyl group per sugar residue on average). The 2, 3 and 6 positions of the monosaccharide units can be independently substituted with an —OH or an —OAc.

Chromatography of Immuno-10 reveals that it contains both polysaccharide and monosaccharide fractions (see FIG. 2). The monosaccharide composition of the activated polysaccharide was determined by high performance anion-exchange chromatography on a Dionex CarboPac PA1 column with pulsed amperometric detection (HPAEC-PAD) using a Dionex Bio-Lc system. Although the immune regulating activity is contained within the polysaccharide peak, the monosaccharides do not affect this activity (data not shown). Immuno-10 may also contain various salts which also do not affect its activity.

Immuno-10 is stable to heat and protease treatments without losing its biological activity, which further indicates that the biological activity of Immuno-10 can be attributed to the activated polysaccharide.

The Immuno-10 isolated by the method of this invention has greater stability than Aloe polysaccharides isolated using previously known methods. Examples 5 and 6 (FIGS. 5–8) illustrate the relationship between the method of processing the polysaccharide and its stability.

This invention also includes the use of Immuno-10 as an immunostimulating, immunomodulating and wound healing agent.

Immunomodulating activity. Immuno-10 restores the UVB-suppressed immune response (contact hypersensitivity); and inhibits UVB-induced Tumor Necrosis Factor α (TNF-α) release from keratinocytes (Human epidermoid carcinoma cells, KB cells).

The local suppression model was used to determine the ability of Immuno-10 to reverse the UVB-suppressed skin immune function, referred to herein as the restorative activity of Immuno-10, as set forth schematically in Example 7. (See, Strickland (1994) J. Invest. Dermatol. 102:197–204 and Vincek et al. (1994) Cancer Research 53:728, which are incorporated herein by reference). In the local suppression model, C3H/HeN mice are exposed to low doses of UVB radiation, which inhibits the induction of the contact hypersensitivity (CH) response to haptens applied at the site of the irradiation. Briefly, the abdominal fur of the mice was shaved and exposed to UVB irradiation at 2000 J/m$^2$, after which Immuno-10 (0.25 mg/mL) in Aquaphor, a known vehicle, was applied to the irradiated area. Three days later the mice were sensitized on the site of irradiation by application of 2,4-dinitrobenzene (DNFB) (0.3%, 50 μL). Six days later the thickness of their ears was measured and then the mice were challenged by application of DNFB (0.2%, 5 μL) to both sides of their ears. Twenty-four hours later the thickness of their ears was measured again. The results are set forth in FIG. 8.

Figure 8:
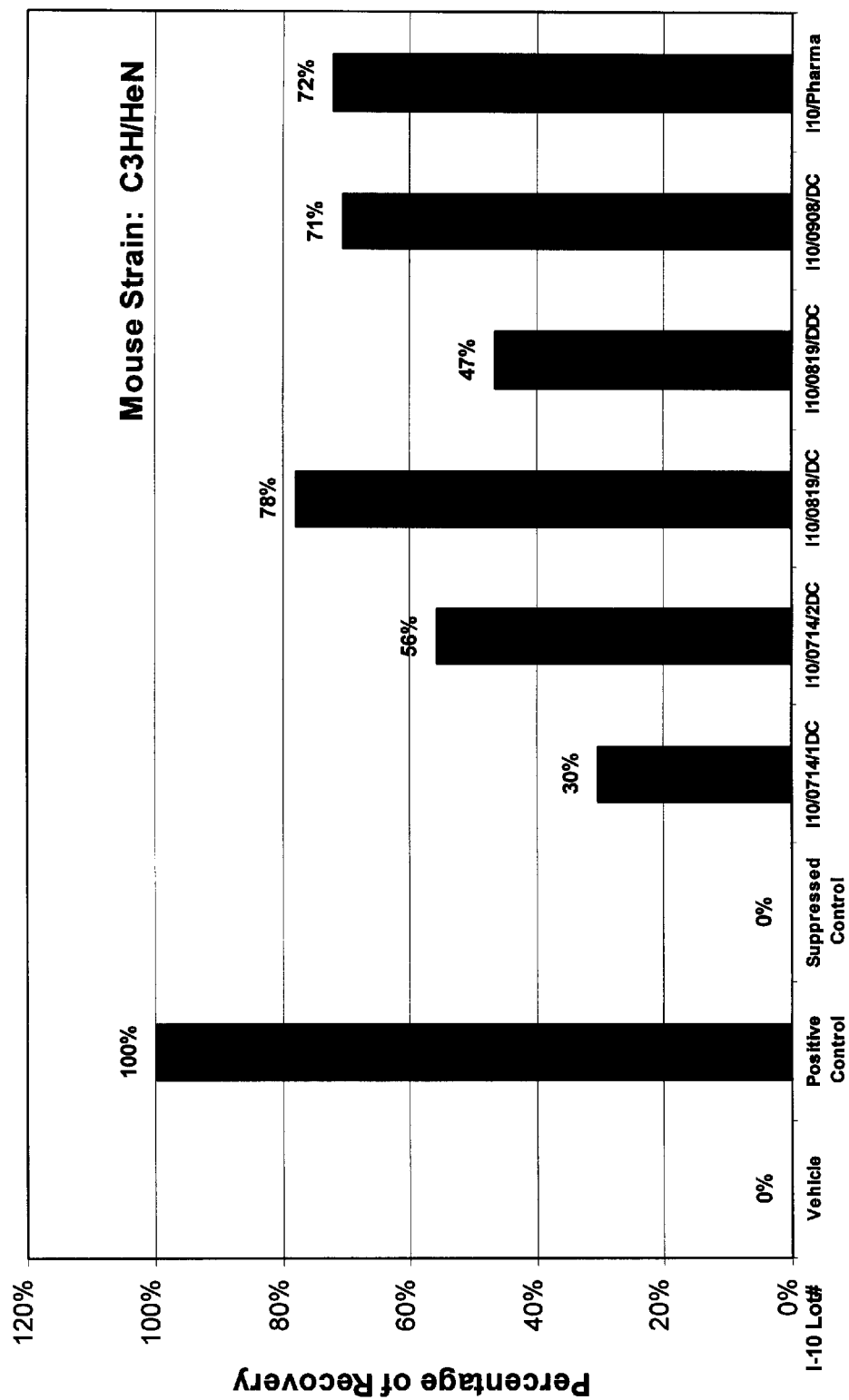
FIG. 8 illustrates graphically the ability of Immuno 10 to restore skin immune function (contact hypersensitivity UVB assay).

In most of the experiments performed, UVB exposure inhibited the CH response by 80~100%. With reference to FIG. 8, this group was used as the negative (suppressed) control (0% CH response). The positive control group of mice received no UVB irradiation and no treatment with Immuno-10 (vehicle only), but were sensitized and challenged (100% CH response). The vehicle (blank) control group of mice received no UVB irradiation, no treatment with Immuno-10 (vehicle only) and no sensitization, but were challenged. This group was used to subtract the net ear swelling caused by any challenge chemical irritation. The Immuno-10 treated groups of mice were treated in the same way as the suppressed control, except that the mice were treated with Immuno-10 in vehicle instead of vehicle only. The percentage of recovery by Immuno-10 was calculated using the following equation:

$$\% \text{ Recovery} = \frac{(A - B)}{(C - B)} \times 100$$

wherein

A=Net ear swelling of Immuno-10 treated group–Net ear swelling of Blank group;

B=Net ear swelling of the Suppressed group–Net ear swelling of the Blank group; and C=Net ear swelling of the Positive group–Net ear swelling of the Blank group.

The higher the percentage of recovery, the more active the Immuno-10. As can be seen in FIG. 8, the activity of Immuno-10 is between 30~80% with an average of about 60%. The immunomodulating activity was stable when Immuno-10 was stored in a solution at 4° C. for 3 months or in a solid form at room temperature for one year.

Figure 9:
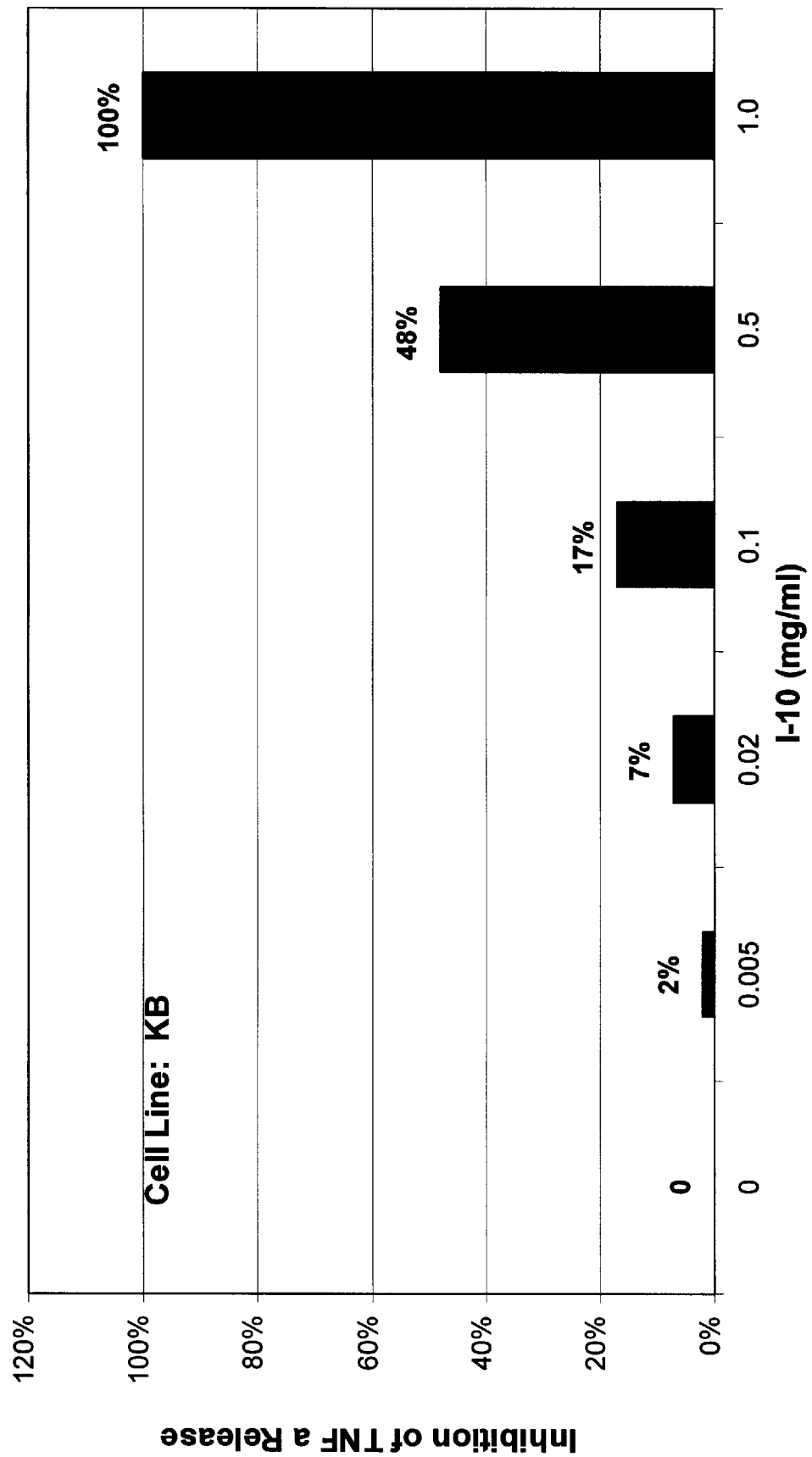
FIG. 9 illustrates graphically the inhibition of UVB irradiation-induced tumor necrosis factor-α (TNF-α) release by Immuno-10.

It has been reported that UVB-induced TNF-α release is involved in the mediation of local immune suppression within the epidermis. An in vitro model was developed to determine the suppression of UVB-induced TNF-α release by Immuno-10. This method is described in Example 8. Human epidermoid carcinoma cell line (KB cells) were used (normal cells do not produce enough TNF-α to be measurable by ELISA). The results are set forth in FIG. 9. The X-axis in FIG. 9 represents the dose of Immuno-10 (mg/mL final concentration in cell media). The Y-axis shows the percentage of inhibition by Immuno-10. The percentage of inhibition by Immuno-10 was calculated using the following formula:

$$\% \text{ Inhibition} = 1 - \frac{(A-B)}{(C-B)} \times 100$$

A=TNF-α amount in the media from the UVB-irradiated and Immuno-10 treated cells;
B=TNF-α amount in the media from the cells without UVB-irradiation; and
C=TNF-α amount in the media from the UVB-irradiated cells, but without Immuno-10 treatment.

As can be seen in FIG. 9, Immuno-10 showed a dose-dependent inhibition of UVB-induced TNF-α release from KB cells. At the concentration of 1 mg/mL, Immuno-10 inhibited the release by almost 100%.

Immunostimulating activity. Immuno-10 activates macrophages by stimulating TNF-α release.

Figure 10:
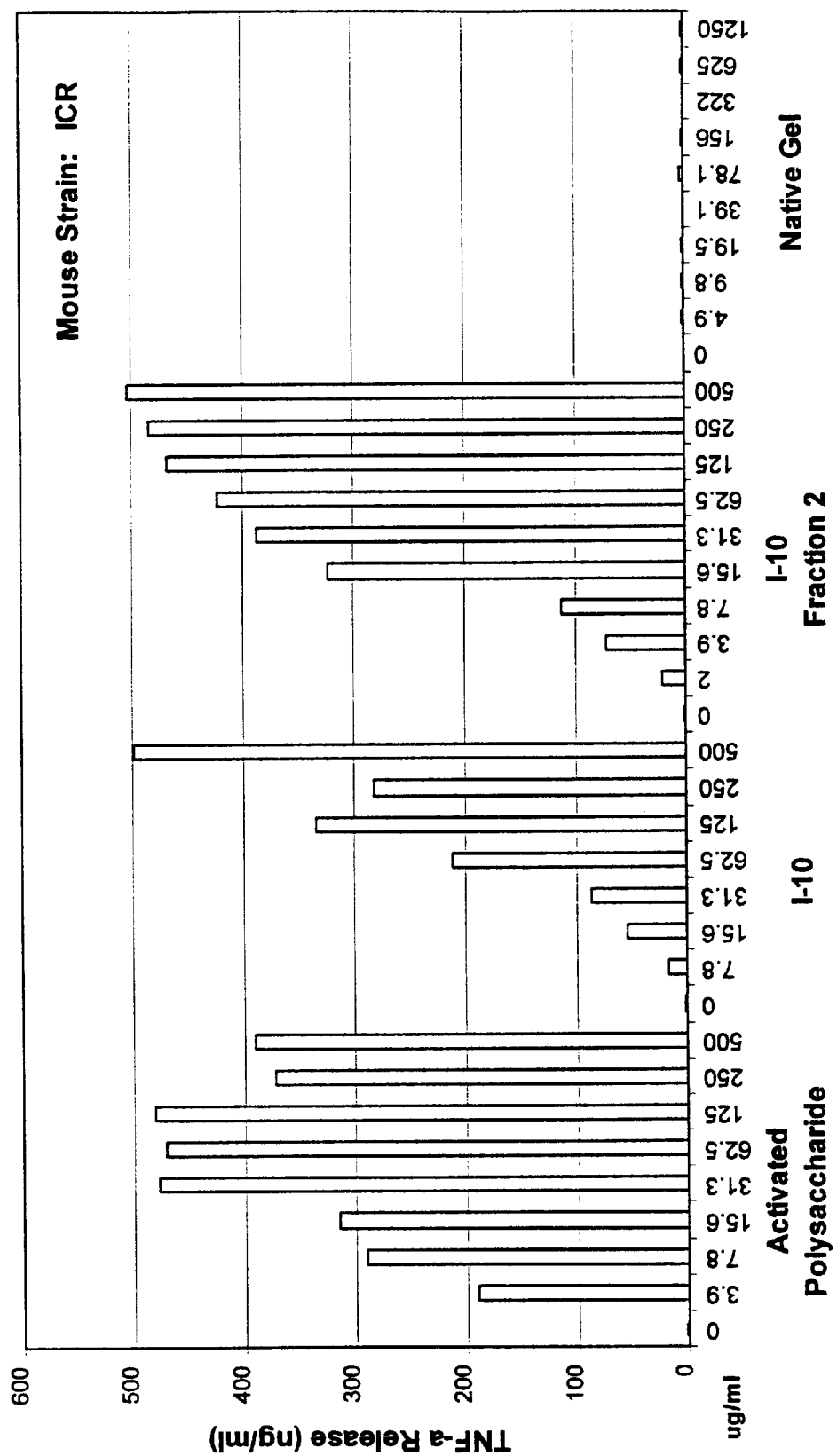
FIG. 10 illustrates graphically the stimulation of TNF-α release from mouse peritoneal macrophages by Immuno-10.

Host defense against malignant tumors consists of several different mechanisms and impairment or failure of immunological defense may lead to the development or progression of malignant disease. Macrophages are antigen-processing cells and have been demonstrated to be both cytotoxic and phagocytic. Each of these functions are significantly enhanced when macrophages are activated. Selective stimulation of this cell population could be important in contributing to the development of therapeutic applications. Activated macrophages are also crucial in the body's ability to heal wounds. Tumor Necrosis Factor α (TNF-α), one of the cytokines released by macrophages, plays a critical role in mediating the signal transduction of the defense system. Example 9 describes the method used to determine Immuno-10 stimulated macrophage activation. The results are set forth in FIG. 10. As shown in FIG. 10, a dose-dependent stimulation of TNF-α release from mouse peritoneal macrophages by Immuno-10 was detected. At the concentration of 0.5 μg Immuno-10 per mL, Immuno-10-stimulated macrophages released 500 times more TNF-α than the unstimulated cells. As can also be seen in FIG. 10, under the same experimental conditions, native Aloe gel did not induce TNF-α release from macrophages. This result indicates that Immuno-10 can be used as both a non-specific stimulator of the immune system and for wound healing.

Wound healing activity. Immuno-10 stimulates fibroblast proliferation (baby hamster kidney cells, BHK-21 cells).

Figure 11:
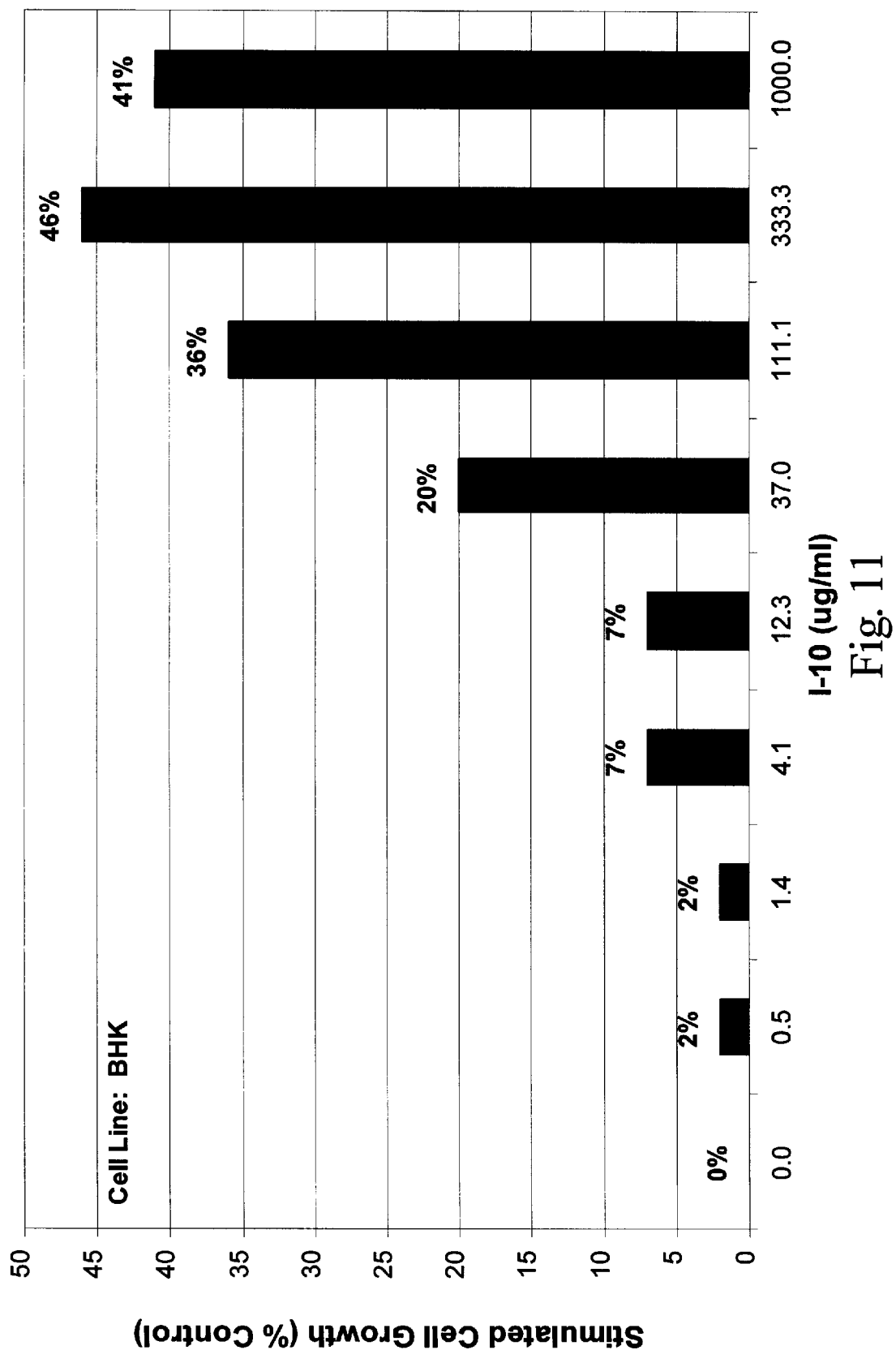
FIG. 11 illustrates graphically the stimulation of cell proliferation by Immuno-10.

Example 10 describes the method used to determine Immuno-10 cell proliferation. The MTT method was used to determine the stimulated cell proliferation. The results are set forth in FIG. 11. As can be seen in FIG. 11, Immuno-10 stimulates BHK-21 cell growth in a dose-dependent manner.

The following examples are provided for illustrative purposes only and are not intended to limit the scope of the invention.

EXAMPLES

Example 1

Isolation and Purification of Immuno-10

Immuno-10 was isolated and purified as outlined in FIG. 1. Briefly, fresh *Aloe barbadensis* gel extract was subjected to limited enzyme digestion at a temperature and for a length of time suitable for limited carbohydrate hydrolysis. This is typically 2 hours at 25° C., using cellulase as the enzyme. The activated Aloe gel was partially purified using activated carbon and filtration (I-10). The activated polysaccharide was then further purified by dialysis, ethanol precipitation and size exclusion chromatography.

Limited Enzyme Digestion

Aloe Gel Juice (AGJ) (10 L) produced from fresh gel fillets (provided by Aloecorp (Harlingen, Tex.)) was heated to 25° C. with a heat exchanger consisting of 60° C. water circulating through a ¼" 316 stainless steel coil while gently mixing with a mechanical agitator equipped with a marine propeller blade (A100). A solution of 116 mg of cellulase 4000 (Valley Research Inc.) in 10 mL of 50 mM aqueous citrate at pH=6 was added and the mixture was gently stirred for 2 hours.

Enzyme Deactivation

After two hours, the reaction mixture was heated to about 90° C. for a minimum of 30 minutes. The reaction mixture was then immersed in an ice-water bath to cool the material to room temperature.

Decolorization and Filtration

Charcoal was used to remove the red color developed during the enzyme deactivation. The material was divided into two 5.0 L batches. To each of the 5.0 L batches, 100.0 g of coarse charcoal (Darco 20×40, purchased from Norit) was added and the mixture gently stirred for one hour at room temperature. Subsequently, 50.0 g of celite 545 (Aldrich Chemical Co.) was added and the slurry stirred for an additional 10 minutes.

The slurry was then pumped into a pressure filter equipped with a 30 μm filter paper (Whatman Grade 113) to remove the solids. The filtrate contained a small amount of fine charcoal particles that channeled through the filter. The material was clarified when filtered over two superimposed filters, a 1.0 μm pore size filter paper (Whatman #1) on top of 0.7 μm filter paper (Whatman GF/F) that were coated with 100 g of celite 545. The filtrate was decolorized and free of fine charcoal particles. The activated polysaccharide was further purified by dialysis, ethanol precipitation and size exclusion chromatography. The filtration data is summarized forth in Tables 1 and 2.

TABLE 1

| First Filtration | |
|---|---|
| Parameter | Value |
| Volume of Slurry | 5 L |
| Filter paper | Whatman #113 |
| Pore Size | 30 μm |
| Filter Aid | None |
| Filtration Area | 113 cm$^2$ |
| Maximum Pressure | <1 psi |
| Average Filtration Rate | 7.0 mL/min/cm$^2$ |
| Liquid Recovery | Quantitative |
| Material Appearance | Contained fine charcoal Particles |

TABLE 2

Second Filtration

| Parameter | Value |
|---|---|
| Volume of Slurry | 5 L |
| Filter paper (combination) | Whatman #1 on top of Whatman GF/F |
| Pore Size | 1.0 μm on top of 0.7 μm |
| Filter Aid | 100 g of Celite 545 |
| Filtration Area | 113 cm$^2$ |
| Maximum Pressure | 2 psi |
| Average Filtration Rate | 0.74 mL/min/cm$^2$ |
| Liquid Recovery | Quantitative |
| Material Appearance | Clear |

Lyophilization

Following filtration the two batches were combined and the material was transferred into lyophilization trays, frozen and lyophilized in a 20 L VirTis Freeze Dryer, to yield 57.14 g of Immuno-10, which is equivalent to 5.71 g of Immuno-10 per liter of AGJ.

Example 2

Preparation of Pharmaceutical Grade Immuno-10 using a Hollow-Fiber Cartridge

Ten grams of freeze-dried Aloe gel was dissolved in 1.8 L of distilled water in a 2 L beaker. The slurry was stirred overnight at 4° C. producing a homogenous mixture. The mixture was filtered through filter paper (Whatman #3) to remove any particulates and the volume of the filtrate was adjusted to 2 L. The mixture was brought to room temperature and a solution of 4.63 mg of cellulase 4000 (Valley Research Inc.) in 5 mL of 50 mM aqueous citrate at pH 6 was added. The filtrate was then pumped through a Hollow-fiber cartridge (UFP-5-E-6, molecular weight cutoff: 5000 Da, A/G Technology Corporation) at an inlet pressure between 10 to 15 psi. Permeate, which had a molecular weight of less than 5,000 Da, was collected in a separate 2 L beaker. The concentrate, which had a molecular weight of greater than 5,000 Da, was collected in the same beaker as the starting filtrate. This mixture was continuously stirred and when the volume of starting filtrate was reduced to one liter, distilled water (1 L) was added to bring the volume back to 2 L. This procedure was repeated 5 times. A total of three 2 L fractions of permeate were collected. The final concentrate was collected as the retained fraction. It took an average of approximately 2.5 hours to collect each 2 L permeate fraction. The fractions were transferred into lyophilization traps, frozen and lyophilized in a 20 L VirTis Freeze Dryer. The yields of the permeate fractions I, II and III, and the retained fraction were 4.88 g, 1.77 g, 0.56 g and 0.37 g, respectively. The retained fraction had the highest activity to restore UVB-suppressed contact hypersensitivity. Fraction III of the permeates had moderate activity to restore UVB-suppressed contact hypersensitivity. Fractions I and II of the permeates were inactive.

Example 3

Process for Preparation of Pharmaceutical Grade Immuno-10

Figure 3:
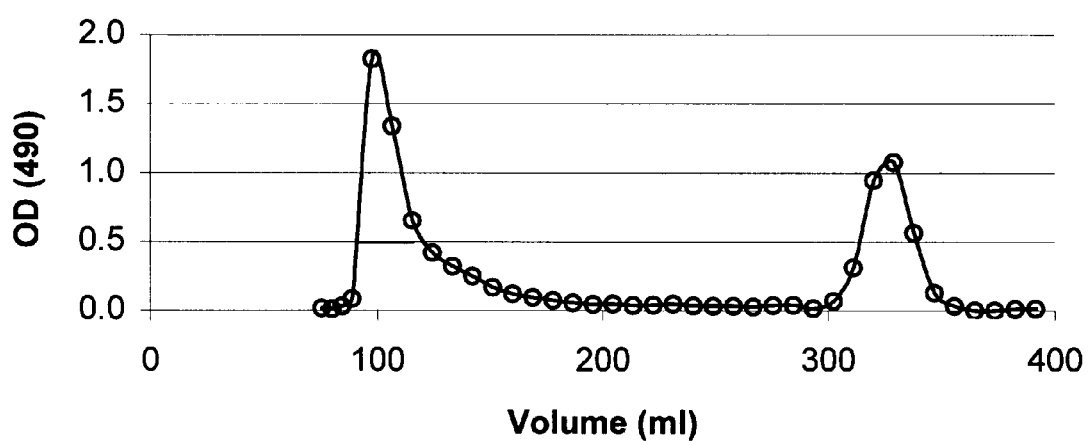
FIG. 3 depicts the chromatogram of partially purified Immuno-10 prepared according to the method of Example 3. The chromatography was performed on a Sephadex G-100 column and absorbance at 490 nm was monitored.

Immuno-10 (50 g), prepared by the method described in Example 1, was dissolved in distilled water (diH$_2$O) to a final volume of 200 mL. Ethanol (66.7 mL, 25% final concentration) was then added to this solution. The addition of ethanol was done slowly while stirring. The solution was then stirred for an additional 30 minutes, during which time a precipitate formed. The mixture was centrifuged at 2500 rpm for 10 minutes (Jouan CR412), and the precipitate was washed once with 25% ethanol, centrifuged and resolublized in diH$_2$O. The resulting solution was lyophilized to dryness (ppt/25%). An additional 133.3 mL of ethanol (25%~50%) was added to the supernatant, as described above, the solution was again stirred for 30 minutes, and the precipitate was collected, washed with 50% ethanol and lyophilized (ppt/25%–50%). This procedure was repeated two more times recrystallizing with 50–75% ethanol (ppt/50%–75%) and 75–80% ethanol (ppt/75%–80%). The solid recoveries of the precipitate for ppt/25%, ppt/25–50%, ppt/50–75% and ppt/75–80% were 0.3%, 20.5%, 10.3% and 1.5%, respectively. The product of ppt/50–75% was further fractionated on a Sephadex G-100 column (2.5×68 cm). The fractions of the polysaccharide peak (left peak, FIG. 3) were combined and lyophilized, to produce pharmaceutical grade Immuno-10. The recovery of the pharmaceutical grade Immuno-10 from the ppt/50–75% was 15.8%.

Example 4

Time Dependant Degradation of Aloe Vera Gel (AJG) Polysaccharide

Figure 4:
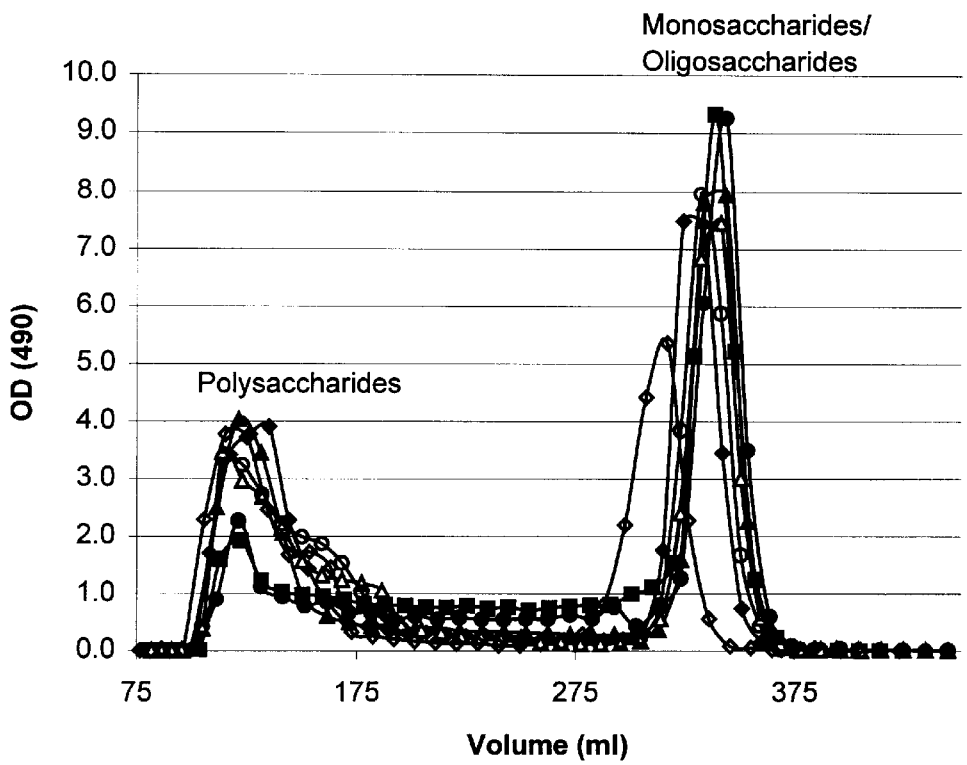
FIG. 4 illustrates the degradation of Aloe polysaccharides by cellulase at 3 minutes (◊),10 minutes (○), 30 minutes (Δ), 60 minutes (♦),120 minutes (▲), 24 hours (●) and 48 hours (■).

Fresh Aloe vera gel extract was treated with cellulase (11.57 mg cellulase per liter of gel extract) at room temperature for 3 minutes, 10 minutes, 30 minutes, 60 minutes, 120 minutes, 24 hours and 48 hours. At the end of the treatment, the gel extracts were heated at 95° C. in a water bath for 30 minutes followed by centrifugation at 2500 rpm for 10 minutes. The supernatants were lyophilized to dryness. The molecular weight distribution of polysaccharides in the treated gel extracts was analyzed by size exclusion chromatography on a Sephadex G-75 column (2.5×68 cm, 177–179 mg of sample was applied to the column). Polysaccharides having a molecular weight ≧75,000 Da eluted at the void volume, while monosaccharides and some oligosaccharides eluted at the column volume (see FIG. 4). The preferred hydrolysis reaction time, based upon biological activity of the resultant product, was determined to be 120 minutes. As can be seen in FIG. 4, treatment with cellulase for 120 minutes resulted in a sharp polysaccharide peak having no shoulder (▲). Treatment with cellulase for 24 hours (●) or 48 hours (■), resulted in a significant decrease in the absorbance of the polysaccharide peak, while the absorbance of the monosaccharide and oligosaccharide peak was increased. The product obtained by treatment for 3 minutes (◇), 10 minutes (○) and 30 minutes (Δ) resulted in a polysaccharide peak having a shoulder.

Example 5

Stability of Aloe Polysaccharide in Different Aloe Preparations

Figure 5:
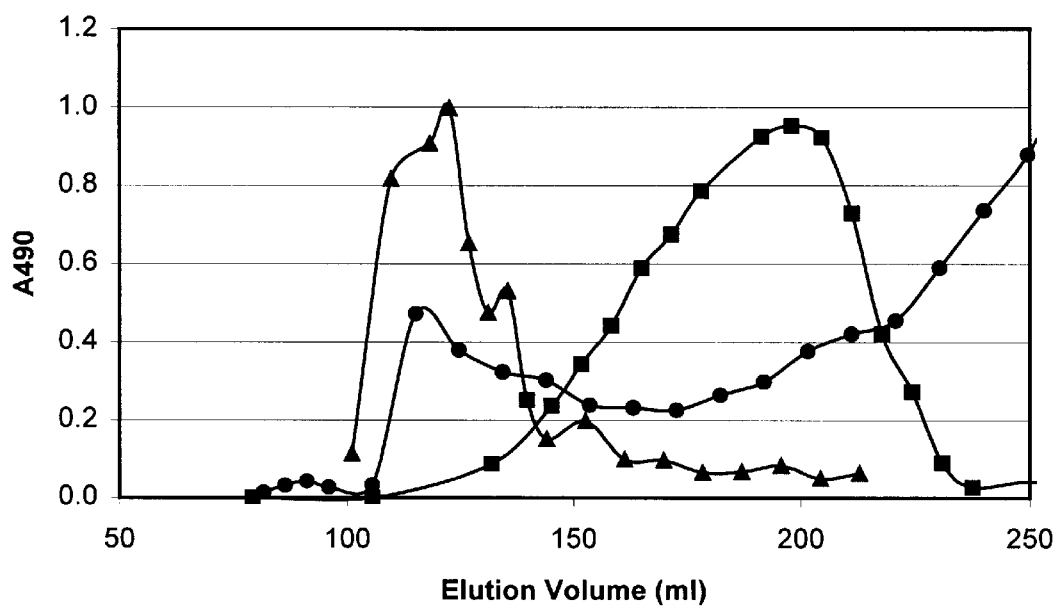
FIG. 5 depicts a chromatogram of Aloe polysaccharide isolated by three different methods: polysaccharide purified from fresh extract using known methods (▲), polysaccharide derived from freeze dried Aloe gel (■) and polysaccharide derived from Aloe whole leaf (●). The chromatography was performed on a Sepharose CL-4B column, monitoring absorbance at 490 nm.

The stability of polysaccharide in fresh Aloe gel extract (purified using standard methods of purification, i.e., dialysis and ethanol precipitation), freeze-dried Aloe gel and freeze-dried Aloe whole leaf was studied by size exclusion chromatography on Sepharose CL-4B column (see FIG. 5). As can be seen in FIG. 5, the Aloe polysaccharide isolated from the fresh Aloe gel extract has a molecular weight of 2 million Da. The polysaccharide in the freeze-dried Aloe whole leaf has a lower molecular weight than that of the polysaccharide isolated from the fresh Aloe gel extract and the polysaccharide in the freeze-dried Aloe gel has a molecular weight of 500,000 Da. This result demonstrates the relationship between the method of processing the polysaccharide and the stability of the Aloe polysaccharide.

Example 6
Stability of Immuno-10 Polysaccharide

Figure 6:
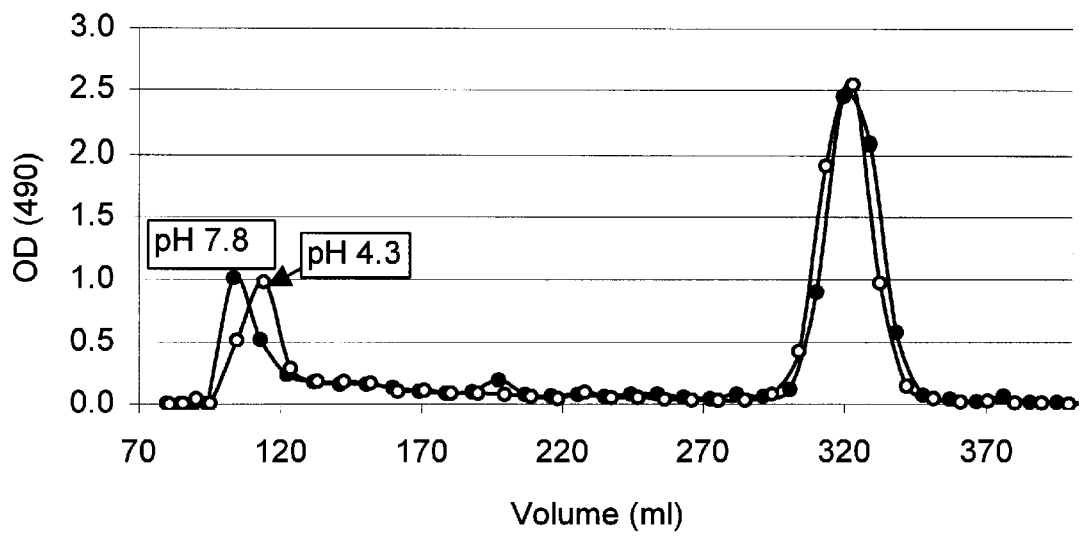
FIG. 6 depicts a chromatogram of Immuno-10 on a Sephadex G-100 column after standing three months in $H_2O$ at pH 4.3 (○) and pH 7.8 (●) at room temperature.
Figure 7:
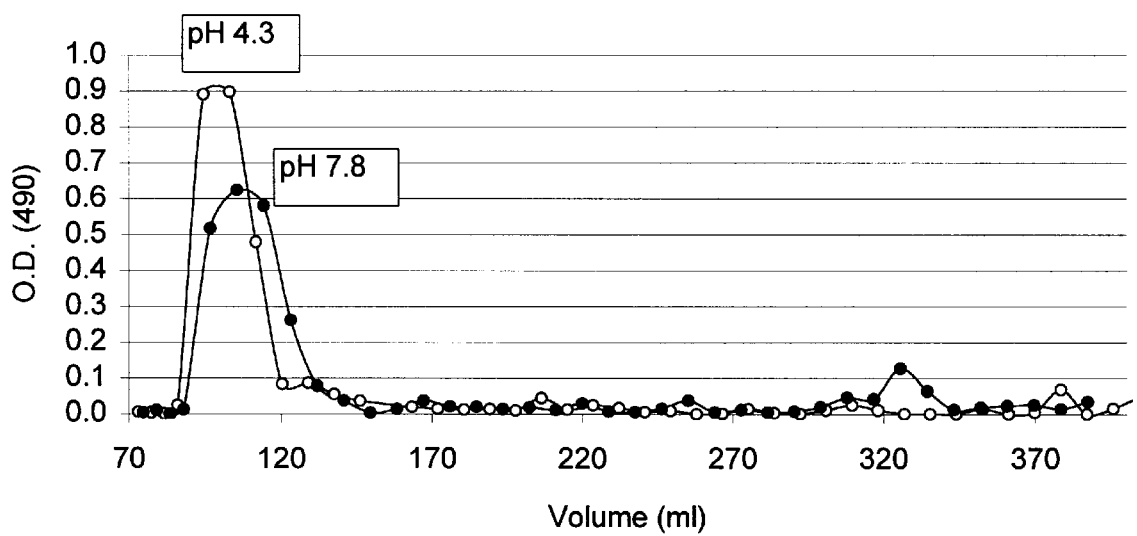
FIG. 7 depicts the chromatogram of purified native Aloe polysaccharide on a Sephadex G-100 column after standing three months in $H_2O$ at pH 4.3 (○) and pH 7.8 (●) at room temperature.

Immuno-10 contains some salts and other small molecules besides polysaccharide. The pH of Immuno-10 in distilled water (diH$_2$O) is about 4.3. To study the stability of Immuno-10 polysaccharide, both purified native Aloe polysaccharide and solutions of Immuno-10 at pH 4.3 or pH 7.8 were left at room temperature for three months. Sodium azide at a final concentration of 0.02% was added to the Immuno-10 or polysaccharide solutions to inhibit microbial growth. The degradation of polysaccharide in these samples was analyzed on Sephadex G-100 column. FIG. 6 depicts the chromatogram showing that the polysaccharide absorbance of Immuno-10 at 490 nm was very similar at both pH 4.3 and pH 7.8. Although the polysaccharide peak shifted slightly to the right side at pH 4.3, it was still very stable under both pH conditions compared with the starting material. Under the same condition, the purified native polysaccharide was partially degraded at pH 7.8 (FIG. 7). The slight shift of the polysaccharide peak could be due to repacking of the Sephadex G-100 column.

Example 7
Determination of Immuno-10 Restored UVB-Suppressed Contact Hypersensitivity Specific-pathogen-free female C3H/HeN mice were obtained from Harlan Sprague Dawley and maintained in a pathogen-free facility in accordance with National Research Council of Laboratory Animal Care guidelines. Each experiment was performed with age-matched mice 9–10 weeks old.

The abdominal hair of mice was removed with electric clippers. The mice having had their ears covered with aluminum foil were then exposed to a bank of four unfiltered FS40 sunlamps (National Biological Corp.) at a dose of 2000 J/m$_2$. Approximately 65% of the energy emitted from these lamps was within the UVB range (280–320) and the peak emission was 313 nm. Immediately after the UVB exposure, Aquaphor (vehicle) alone or tested compound in Aquaphor at a 1:1 ratio was applied onto the abdominal skin of the mice. The mice were then sensitized on their shaved abdominal skin with 50 $\mu$L of 0.3% dinitrofluorobenzene (DNFB), 3 days after the UVB exposure. Six days after sensitization, the mice were challenged by painting 5 $\mu$L of 0.2% DNFB on both the dorsal and ventral surface of each ear. Ear thickness was measured using an engineers' micrometer immediately before challenge and 24 hours later. Specific ear swelling was determined by subtracting values obtained from mice that were challenged but not sensitized (blank group). Each treatment group contained five mice. Two additional control groups were included in each experiment—a positive control group and a suppressed group. The positive control received no UVB radiation and no treatment, but sensitized and challenged (100% response). The suppressed group of mice received UVB radiation and no treatment, but were sensitized and challenged (0% response). The results are set forth in FIG. 8.

Example 8
Determination of Immuno-10 Suppressed UVB-induced TNF-$\alpha$ Release Human epidermoid carcinoma cells (KB) were plated at 2×10$^6$ cells per 100 mm dish. After the cells reached confluence (about 2 days), they were washed three times with PBS and exposed to UVB radiation at 300 J/m$_2$. The cells were then washed once with PBS and incubated in 5 mL DMEM/0.2% FBS with or without Immuno-10 for 1 hour. The cells were washed once more with PBS and further incubated in a growth medium overnight. The next day the medium was collected and centrifuged at 2500 rpm for 10 minutes at 4° C. The TNF-$\alpha$ released into the supernatant was determined by ELISA. The results are set forth in FIG. 9.

Example 9
Determination of Immuno-10 Stimulated Macrophage Activation

Resident mouse peritoneal macrophages were isolated from ICR mice and plated at 200,000 cells per well in a 96-well plate. The cells were washed three times to remove non-adherent cells after a 2 hour incubation. Macrophages were then incubated with or without Immuno-10 overnight. The TNF-$\alpha$ released into the media was determined by ELISA. Lipopolysaccharides (LPS) were used as a positive control. The results are set forth in FIG. 10.

Example 10
Determination of Immuno-10 Stimulated Cell Proliferation (MTT)

Baby hamster kidney cell line (BHK cells) were plated at 5000 cells per well in a 96well plate. The cells were incubated with or without Immuno-10 for 3 days in the tissue culture incubator. The cells were then incubated with 1 mg/mL MTT (3-(4,5-dimethylthiazol-2-yl)-2,3-diphenyltetrazolium bromide, Thiazolyl blue) for 4.5 hours. The absorbance at 570–630 nm was determined after the cells were extracted with 100 $\mu$L of 10% SD in 0.01N HCl. Fibroblast growth factor (FGF) was included as a positive control. The results are set forth in FIG. 11.

What is claimed is:

1. A composition of matter comprised primarily (>95%) of polysaccharides derived from Aloe having the following characteristics:
   (a) said polysaccharides in said composition have an average molecular weight of 70–80 kDa with a range between 50–200 kDa;
   (b) said polysaccharides in said composition are comprised of D-galactose (approx. 5% or less), D-glucose (approx. 5% or less) and D-mannose (approximately 90%);
   (c) said polysaccharides in said composition are comprised of monosaccharides having primarily $\beta$-1,4 linkages; and
   (d) said polysaccharides in said composition are highly acetylated having approximately 1 acetyl group per monosaccharide, wherein said acetyl group is on the 2, 3 or 6 position of the monosaccharide unit.

2. The composition of matter of claim 1 wherein said polysaccharides are also comprised of trace amounts of xylose and arabinose.

3. The composition of claim 1 wherein said polysaccharides are comprised of D-galactose and D-mannose in a ratio of 1 to 9.6±2.2.

4. The composition of matter of claim 1, prepared according to a method comprising:
   (a) extracting Aloe gel juice from said Aloe species;
   (b) performing a controlled limited enzymatic hydrolysis of total polysaccharide in said Aloe gel juice, at a temperature and for a period of time suitable for controlled limited carbohydrate hydrolysis;
   (c) terminating said controlled limited hydrolysis; and
   (d) optionally decolorizing and filtering said Aloe gel juice.

* * * * *